United States Patent [19]
Kula et al.

[11] Patent Number: 5,155,040
[45] Date of Patent: Oct. 13, 1992

[54] PROCESS FOR REDUCING THE SALT CONCENTRATION IN A BIOMASS SUSPENSION

[75] Inventors: Maria-Regina Kula, Niederzier-Hambach; Arend Greve, Vallendar, both of Fed. Rep. of Germany

[73] Assignee: Forschungszentrum Juelich GmbH, Juelich, Fed. Rep. of Germany

[21] Appl. No.: 493,122

[22] Filed: Mar. 15, 1990

[30] Foreign Application Priority Data

Mar. 15, 1989 [DE] Fed. Rep. of Germany ....... 3908421

[51] Int. Cl.$^5$ ............................. C07K 3/00; C07K 3/02
[52] U.S. Cl. .................................... 435/247; 435/183; 435/255; 435/256; 435/261; 210/634; 210/767; 530/424
[58] Field of Search ............... 435/247, 255, 256, 261, 435/803, 804, 183; 530/424; 210/634, 767

[56] References Cited

U.S. PATENT DOCUMENTS 3,844,893 10/1974 Hitzman .............................. 195/115
4,816,407 3/1989 Matson ................................ 435/287

OTHER PUBLICATIONS

T. Maniatis, et al., "Molecular Cloning a Laboratory Manual", Cold Spring Harbor Laboratory, pp. 461-462, (1982).

Primary Examiner—Merrell C. Cashion, Jr.
Assistant Examiner—Andrew G. Rozycki
Attorney, Agent, or Firm—Foley & Lardner

[57] ABSTRACT

Alcohol is suitable for the extraction of salt from biomass-containing suspensions, in particular from the salt-containing lower phase of an aqueous 2-phase extraction of intracellular proteins after cell disruption, with the formation of a salt-containing alcoholic upper phase. It is possible to use ethanol, propanol, isopropanol or tert.-butanol, but especially ethanol, as the alcohol. The upper phase is separated from the lower phase by disk separators or decanters. The extraction is carried out, in particular, as a countercurrent extraction in at least three stages, and uses 10 to 30% by weight salt-containing suspension or liquid with 30 to 50% by weight alcohol, in particular ethanol, remainder water. The alcohol is removed from the resulting salt-rich upper phase by evaporation, and the salt solution is recycled where appropriate after further concentration to obtain proteins.

13 Claims, 5 Drawing Sheets

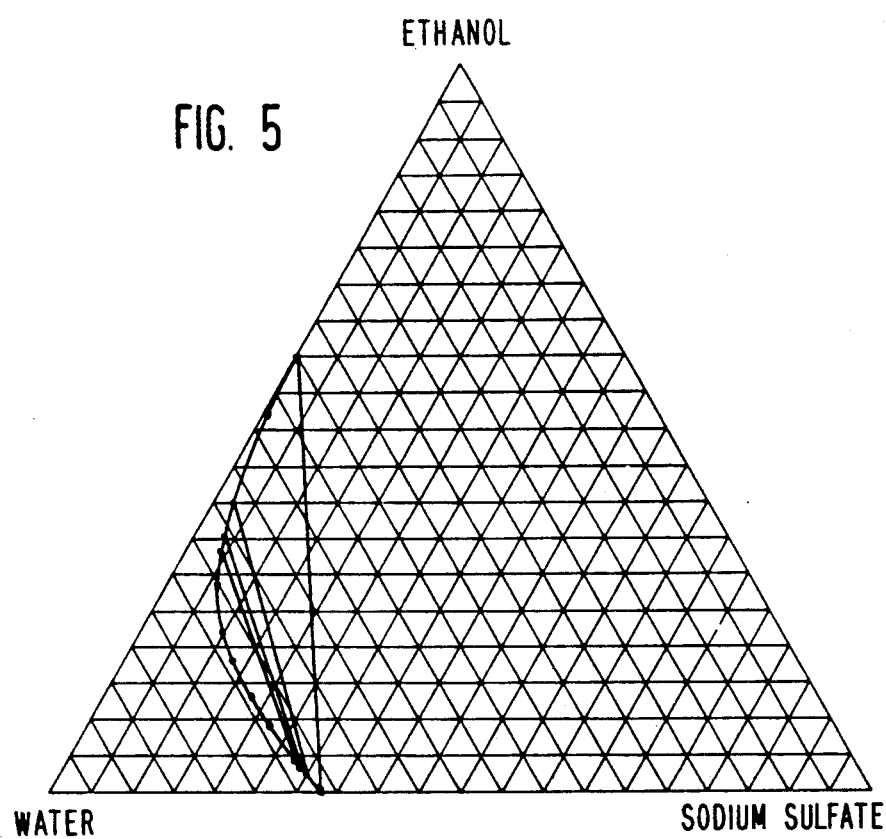
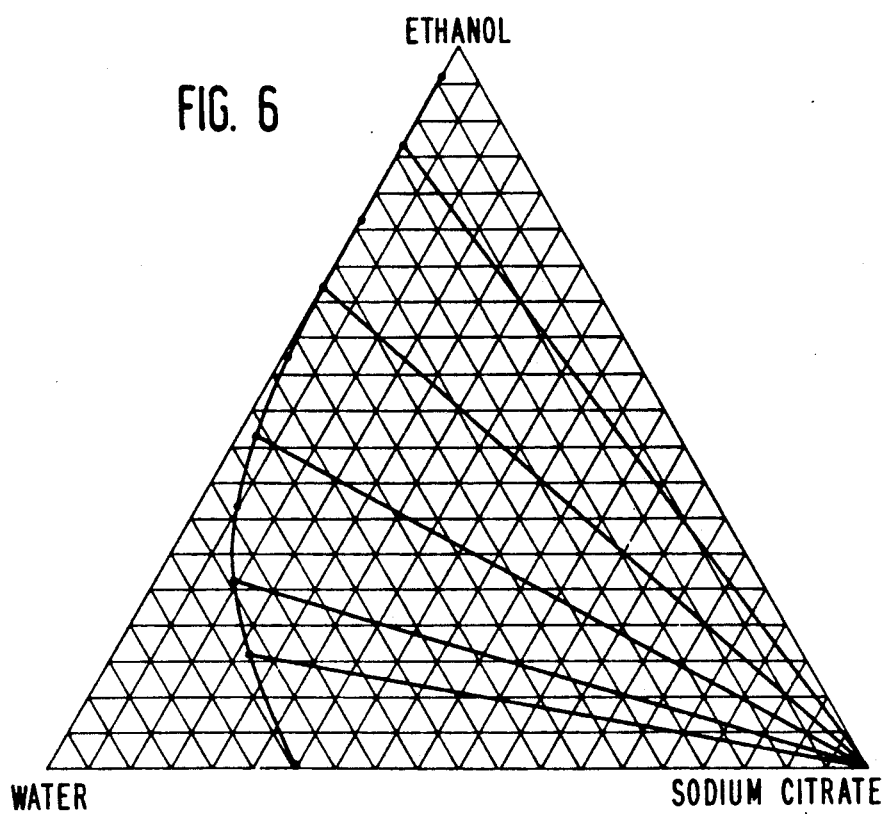

PROCESS FOR REDUCING THE SALT CONCENTRATION IN A BIOMASS SUSPENSION

BACKGROUND OF THE INVENTION

The present invention relates to a process for reducing the salt concentration in a biomass-containing suspension, in a particular in a liquid containing cell fragments for obtaining proteins.

When obtaining intracellular proteins, disruption of the cells is followed by the use of aqueous phase systems composed of polyethylene glycol (PEG) and salt (phosphates, sulfates or citrates) in order to separate the cell fragments from the proteins and to concentrate the proteins. Aqueous solutions of polymer and salt (e.g., PEG with a molecular weight of 1,000–10,000 and potassium phosphate) separate above limiting concentrations into aqueous phases. Proteins, cells and cell fragments may be distributed differently in these phases depending on the concentration of the phase-forming substances. It is possible, by suitable choice of the phase system, to separate the cell fragments from the desired protein and to purify this protein further (M.-R. Kula et al., *Adv. Biochem. Eng.* 24:73–118 and German Patent 26 39 129).

This results in waste material in the form of a generally viscous suspension which contains cell fragments and in which between 10 and 25% (w/w) salt are dissolved, besides high molecular weight nucleic acids and soluble and insoluble protein. The salt should be recovered from this biomass-containing suspension in order both to reduce the costs of reagents and to minimize environmental pollution.

Since the cell fragments have a particle size between 0.05 and 5 μm (lower limit not fixed), a small difference in density from the surrounding liquid, and cause a high viscosity, it is difficult to remove the salt mechanically. Available known processes are microfiltration, electrodialysis or heat-agglomeration of the lower phase, but implementation of these is not entirely satisfactory.

In the case of microfiltration, in view of the small particle size, it is necessary to use membranes with a very small effective separation size, in which case even with pressure differences of 1 bar across the membrane and flow-over rates of 5 m/s, the maximum flow rates achieved are only about 25 l/m².h.

In the case of electrodialysis of such suspensions, the limiting current density decreases considerably as a consequence of formation of top layers composed of cell fragments on the diluate side of the membrane so that continuous operation is not technically achievable.

Even heat-agglomeration and separation of the agglomerate encounters considerable difficulties, especially separation problems, so that the use of this process is likewise unfeasible.

SUMMARY OF THE INVENTION

It is therefore an object of the invention to provide a process for reducing the salt concentration in a biomass-containing suspension, in particular in the salt-containing lower phase of an aqueous two-phase extraction of intercellular proteins after cell disruption, which can be used commercially without difficulties.

In accordance with these and other objects according to the present invention, a process is provided for reducing the salt concentration in a biomass-containing suspension, comprising the steps of providing a biomass-containing suspension, extracting salt from the suspension with alcohol, in forming a salt-containing alcoholic upper phase.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 5 is a triangular diagram for ethanol, sodium sulfate, and water.

FIG. 6 is a triangular diagram for ethanol, sodium citrate, and water.

DETAILED DESCRIPTION OF THE PREFERRED EMBODIMENTS

The process developed according to the invention comprises extraction of salt with alcohol from a biomass-containing suspension or liquid, with the formation of a salt-containing alcoholic upper phase.

As has been found, alcohol/water/salt systems of water-soluble alcohols separate into two phases at a particular composition, with cell fragments remaining in the lower phase. The salt is distributed between the lower phase and upper phase and can be removed, in one or more stage(s), from the biomass-containing lower phase to an extent which is at least sufficient for disposal of the latter to pose no problems.

In this connection, it is possible to use any alcohol which is miscible with water, but which is itself unable to dissolve the salt.

The following alcohols have been investigated in particular:
methanol
ethanol
1-propanol
2-propanol
tert.-butanol.

Methanol probably has less practical importance because of its low boiling point, the relatively high concentrations required to form 2-phase systems and its high heat of vaporization, the highest within the alcohol group. Triangular diagrams for the other alcohols have been constructed at 25° C. and using potassium phosphate pH7 (a mixture of $KH_2PO_4$ and $K_2HPO_4$). This salt was chosen because it is the salt most often used in obtaining proteins (see FIGS. 1–4). The utility of the process for other salts was demonstrated, and sodium sulfate and sodium citrate are exemplified in FIGS. 5 and 6.

Since tert.-butanol is toxic and has a relatively high melting point (25.5° C.), and isopropanol is more costly, 1-propanol and ethanol are preferred. More extensive investigation was carried out on 1-propanol and ethanol, especially ethanol.

It is most expedient to use mixtures which in the 2-phase zone are near the critical point, where the upper and lower phase compositions are approximately the same, so that a maximum reduction in the salt concentration in the biomass-containing lower phase is achieved.

The useful working range of the process using ethanol is apparent from the attached plots (FIGS. 7 and 8) for the biomass-containing model system: 20% (w/w) *S. cerevisiae*, 18% (w/w) PEG 1500 and 7% (w/w) potassium phosphate pH7.

Important parameters for extraction of the salt in practice are:
a sufficiently large difference in density between the phases to be separated;
separation of the phases in individual stages of a multistage extraction in a constant ratio by volume and a clear upper phase,
but the yield after one stage or the number of theoretical stages is particularly important. The alcohol is normally added as an aqueous solution to the system.

Figure 1:
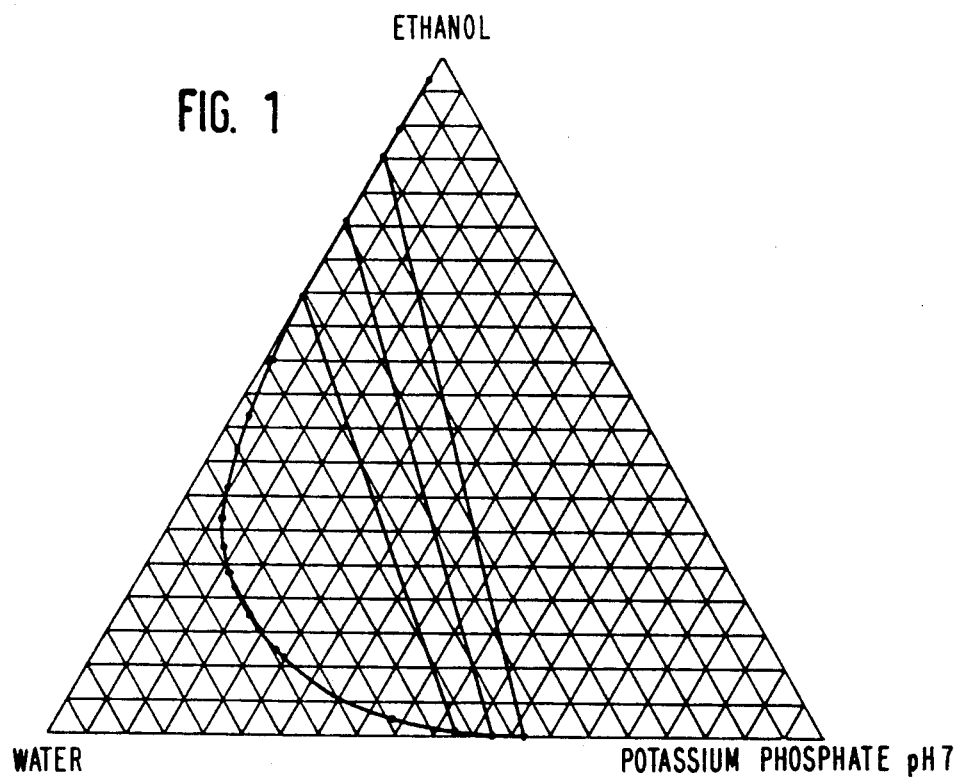
FIG. 1 is a triangular diagram for ethanol, potassium phosphate (pH7), and water.
Figure 2:
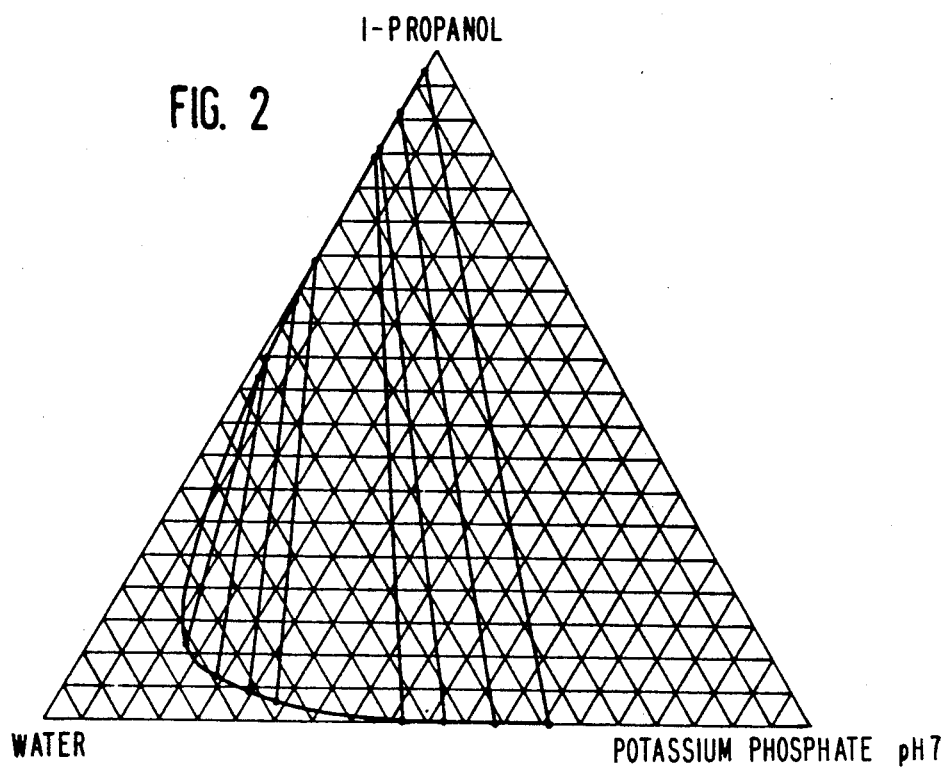
FIG. 2 is a triangular diagram for 1-propanol, potassium phosphate (pH7), and water.
Figure 3:
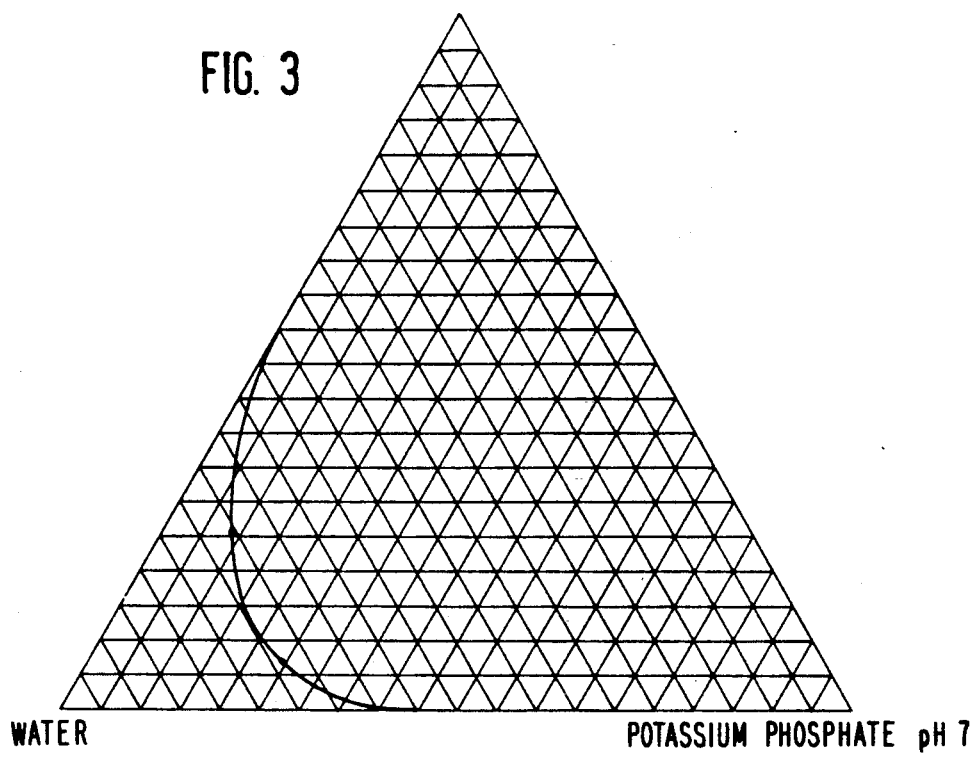
FIG. 3 is a triangular diagram for 2-propanol, potassium phosphate (pH7), and water.
Figure 4:
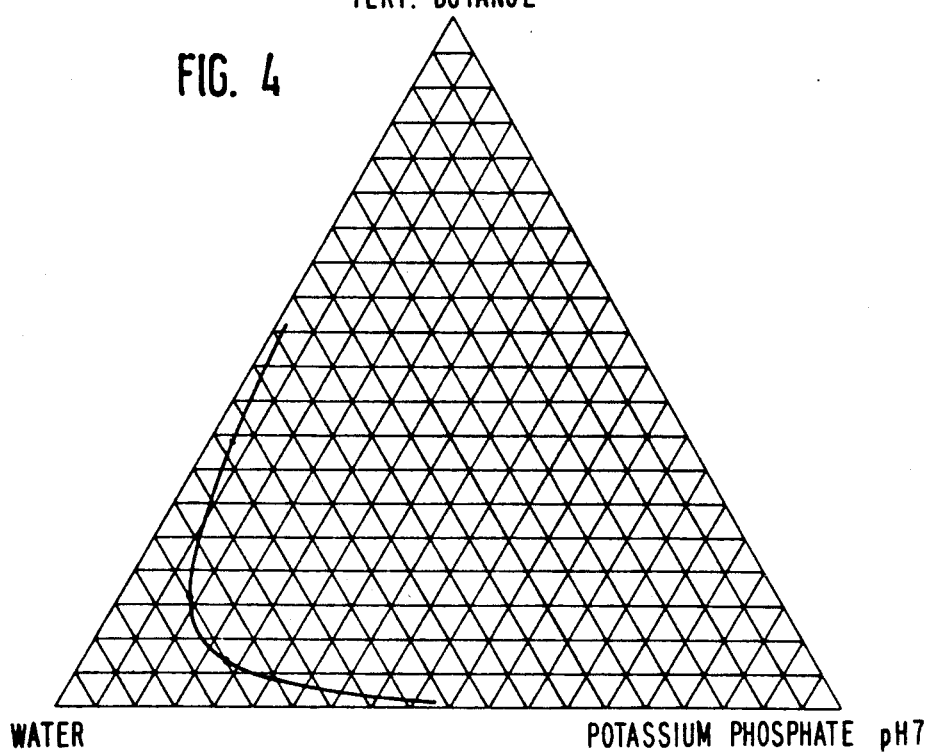
FIG. 4 is a triangular diagram for tert.-butanol, potassium phosphate (pH7), and water.
Figure 7:
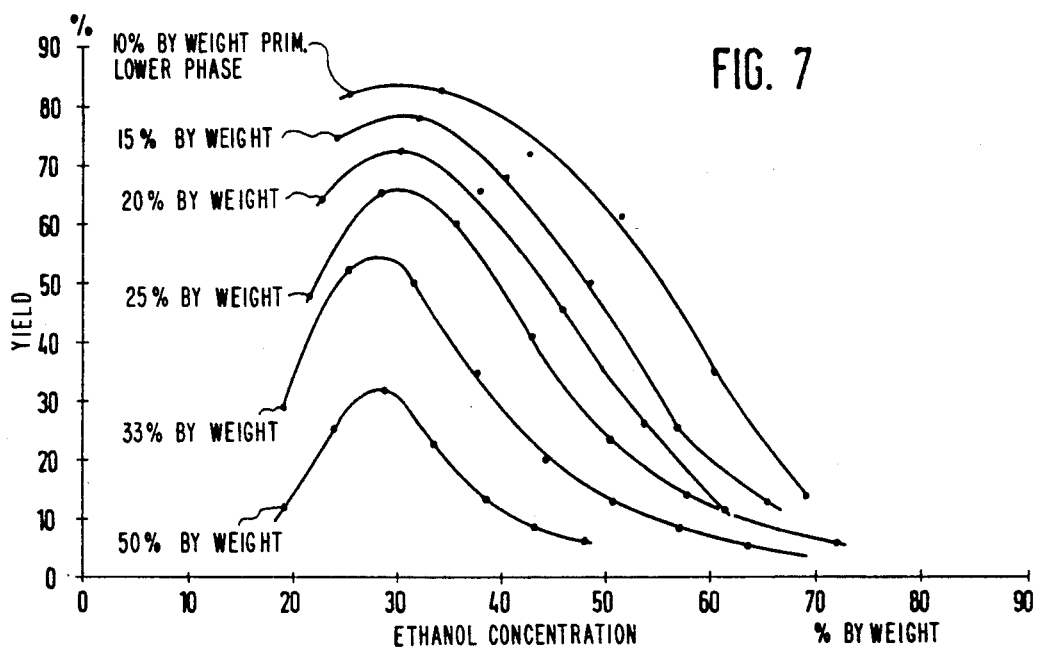
FIG. 7 shows yield as a function of ethanol concentration.
Figure 8:
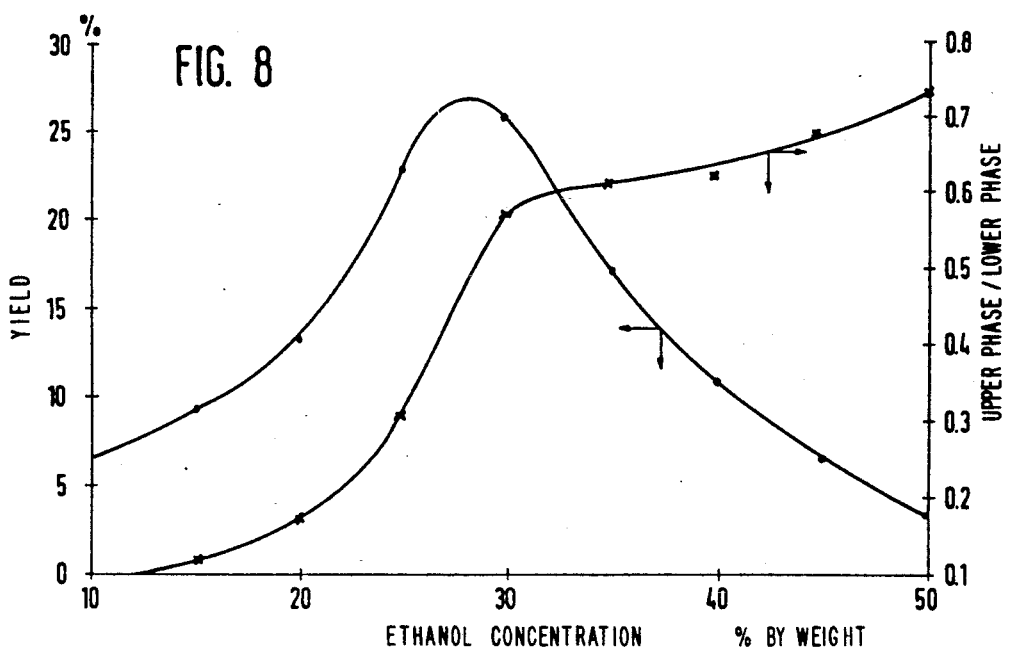
FIG. 8 shows the effect, at a proportion of 50% by weight suspension, of the alcohol concentration on the phase separation.

It can be seen from FIGS. 7 and 8 that a 95% (w/w) removal of potassium phosphate is possible in three to four theoretical stages in the case of countercurrent separation using mixing ratios of 30-40% (w/w) ethanol in the complete system and a proportion of the biomass-containing suspension ("primary lower phase") of 15-25% (w/w). The remainder is water.

FIG. 7 shows the yield (i.e., the proportion of salt in the upper phase related to the total amount of salt after one separation stage) as a function of the ethanol concentration (in % by weight of the mixture of upper and lower phase), where the parameters chosen were the proportions of biomass-containing suspension in % by weight. The family of curves shows that an optimal transfer of salt into the upper phase is achieved when the proportion of suspension is minimized. However, as the proportion of biomass decreases the amount of salt which can be removed per separation stage decreases so that it is expedient to use proportions of at least 15% by weight suspension.

FIG. 8 shows the effect, at a proportion of 50% by weight suspension, of the alcohol concentration on the phase separation, which is characterized by the ratio of upper to lower phase by mass, and the yield. It is seen that at and above a proportion of about 30% by weight ethanol in a total mixture a clear phase separation is achieved with an approximately constant ratio of upper to lower phase by mass.

Since the yield decreases above 30% by weight ethanol, it is preferable to work near this concentration.

These relationships are somewhat affected by the nature of the biomass. Thus, the proportions of alcohol used for extractions of salts from yeast-containing systems are somewhat lower than in the case of bacteria-containing systems. In general, it is particularly expedient for the proportions of alcohol to be 30-50% for proportions of cell suspension between 10 and 30%, remainder water.

The process according to the invention was developed especially in connection with obtaining intracellular proteins by phase distribution. However, it is equally useful for other processes where liquids or suspensions of biomass or proteins with a high salt load are produced.

In this connection, the proportion of cell suspension is determined, on the one hand, by considerations of cost and, on the other hand, by the requirement for adequate salt extraction; the costs for the process increase if the proportion of cell suspension is too low, whereas adequate salt extraction is no longer possible where the proportion of cell suspension is too high.

The proportions of alcohol are essentially determined by the desired success of salt removal. Thus, in the exemplified system with proportions below 30% alcohol there is no longer adequate phase separation, whereas with proportions above 50% alcohol there is too little water in the upper phase, which has an adverse effect on salt removal.

Figure 9:
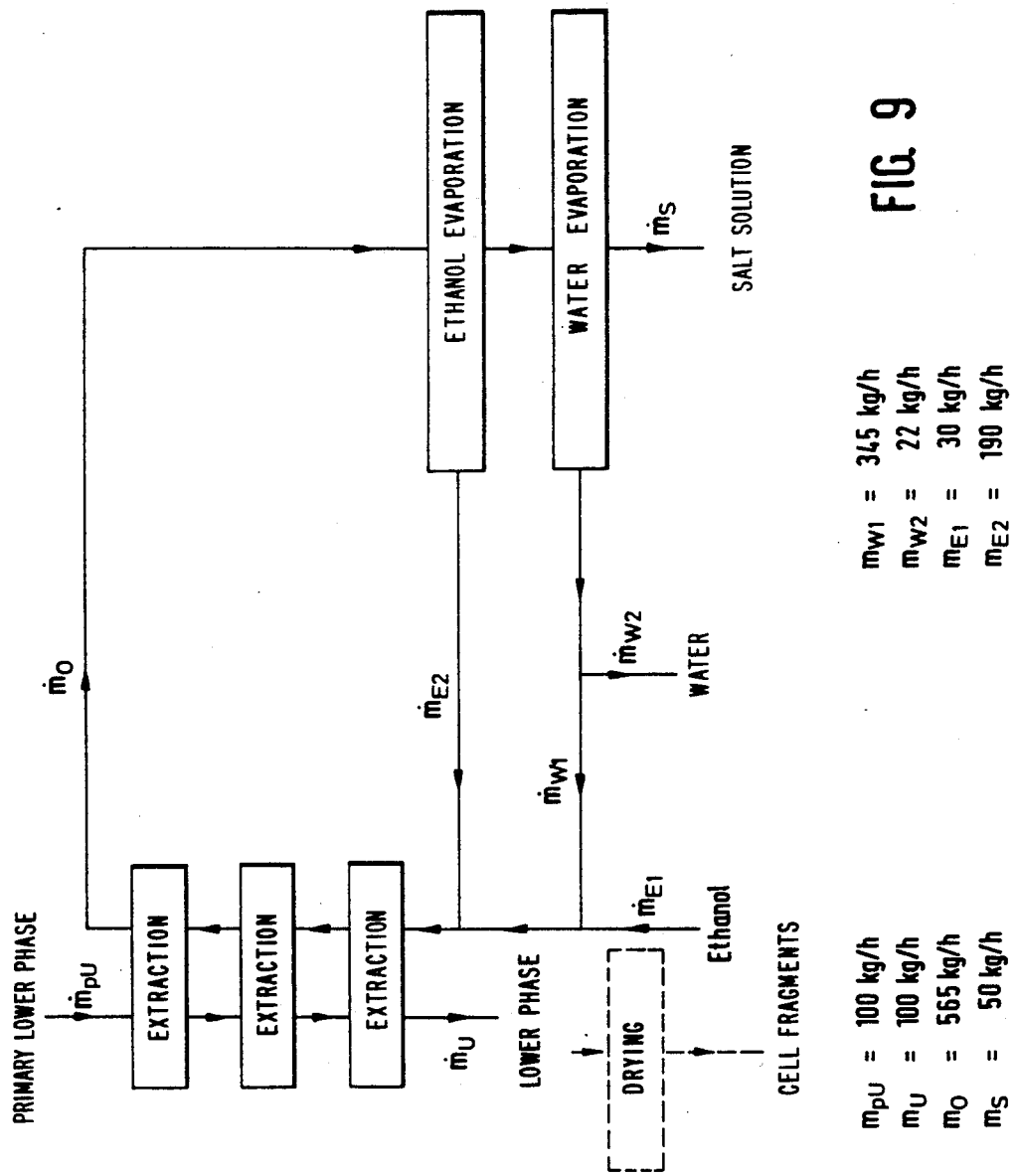
FIG. 9 is a schematic diagram of the process according to the present invention.

The attached FIG. 9 shows a diagram for practical application of the process according to the invention for reducing the salt concentration in the biomass-containing phase, there also being obtained, after evaporation of the alcohol and of water, a salt solution which can be recycled to obtain the protein. The alcohol and part of the evaporated water are returned to the salt extraction where the primary lower phase (biomass-containing suspension) and aqueous alcohol solution undergo three countercurrent extraction stages.

What is claimed is:

1. A process for reducing the salt concentration in a biomass-containing suspension, comprising the steps of:
   providing a biomass-containing suspension,
   extracting salt from the suspension with an alcohol which is miscible with water, but which is itself unable to dissolve the salt, and
   forming a salt-containing alcoholic upper phase.

2. A process as claimed in claim 1, wherein the alcohol is selected from the group consisting of ethanol, propanol, isopropanol and tert.-butanol.

3. A process as claimed in claim 1, wherein the biomass-containing suspension comprises cell fragments for obtaining intracellular proteins.

4. A process as claimed in claim 3, wherein the extraction produces a lower phase which contains cell fragments, soluble and insoluble protein, nucleic acid and salt.

5. A process as claimed in claim 4, wherein the extraction is an aqueous two-phase extraction.

6. A process as claimed in claim 3, wherein the intracellular proteins are enzymes.

7. A process as claimed in claim 1, wherein the extraction mixture comprises 10 to 30% by weight of salt-containing suspension or liquid, 30 to 50% by weight of alcohol, and the remainder water.

8. A process as claimed in claim 4, wherein the extraction is carried out in consecutive stages.

9. A process as claimed in claim 8, wherein the extraction is a countercurrent extraction in at least three stages.

10. A process as claimed in claim 1, wherein the separation of the upper phase from the lower phase is effected by disk separators or decanters.

11. A process as claimed in claim 1, wherein the alcohol is removed from the resulting salt-rich upper phase by evaporation, and the salt solution is recycled.

12. A process as claimed in claim 2, wherein the alcohol is selected from the group consisting of propanol and ethanol.

13. A process as claimed in claim 12, wherein the alcohol is ethanol.

* * * * *